(12) United States Patent
Smith et al.

(10) Patent No.: US 7,576,346 B1
(45) Date of Patent: Aug. 18, 2009

(54) USE OF SOLAR ILLUMINATION AND BAFFLES TO CALIBRATE VISIBLE SENSORS

(75) Inventors: David Stanley Smith, Fort Wayne, IN (US); Douglas Lent Cohen, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 70 days.

(21) Appl. No.: 11/865,200

(22) Filed: Oct. 1, 2007

(51) Int. Cl.
*G01N 21/86* (2006.01)

(52) U.S. Cl. .................................. 250/559.1; 250/203.4

(58) Field of Classification Search .............. 250/559.1, 250/203.4, 203.6, 206.1, 208.1, 216; 359/399, 359/729, 894; 126/620–623, 680–690, 696–702, 126/573

See application file for complete search history.

(56) References Cited

U.S. PATENT DOCUMENTS 4,279,240 A * 7/1981 Artusy ....................... 126/579

OTHER PUBLICATIONS

Pages 109-110 of Radiation Heat Transfer by E.M. Sparrow and C.D. Cess (Augmented Edition, Hemisphere Publishing Company, New York, 1978).

* cited by examiner

*Primary Examiner*—Que T Le
(74) *Attorney, Agent, or Firm*—Ratner Prestia

(57) ABSTRACT

A device for calibrating a sensor using solar radiation includes a sensor configured to measure electromagnetic radiation received through a field of view (FOV) having a normal line of sight and at least two baffles removably insertable across the FOV of the sensor and inclined to the line of sight. Each baffle has first and second opposing surfaces, with the first surface disposed to face the solar radiation and the second surface disposed to face the sensor. One of the first or second surface is configured as a diffused surface, and the other of the first or second surface is configured as a specular surface.

20 Claims, 14 Drawing Sheets

USE OF SOLAR ILLUMINATION AND BAFFLES TO CALIBRATE VISIBLE SENSORS

FIELD OF THE INVENTION

The present invention relates to a system and method for calibrating a sensor using solar radiation. More specifically, the present invention relates to using solar radiation to calibrate an imaging sensor disposed in an orbiting satellite.

BACKGROUND OF THE INVENTION

Spacecraft such as satellites generally support devices having energy detecting capabilities of one type or another. Typical remote sensing devices provide measurement of reflected (primarily solar) or emitted (from man-made sources) visible and near-infrared energy from the Earth or other heavenly bodies. A method of calibrating the measured radiance from Earth (or another source) is to create a reference radiance using a ubiquitous, known source of spectral irradiance, such as the Sun, as reference input to a diffusive reflector that provides a known radiance to the remote sensing instrument.

The standard radiance value may be created by reflecting known solar spectral irradiance from a diffuser panel toward the remote sensing device during an occasional (non-normal operation) calibration. The remote sensing device output is measured as the device receives the known diffusely reflected energy from the diffuser panel. Using the characteristics of the remote sensing device and a reference view of empty space (i.e. no significant irradiance at the remote sensing device), response of the device to known radiance input is determined. This calibration process provides sufficient information to calculate radiance incident to the remote sensing device during normal operation using the instrument output as it views the Earth or other targets of interest.

For example, imagers and other sensors in earth orbit that measure electromagnetic radiation at wavelengths between 0.3 and 0.7 microns (the visible band), such as the Landsat satellite program, are often calibrated using solar radiation reflected off a diffusely reflective surface, as shown in FIG. 1. The sensor in FIG. 1 is represented schematically by single lens 12 focusing an image onto detector array 14. The sensor is calibrated by swinging diffusely reflecting surface 10, often a lambertian surface, into a blocking position over the sensor aperture. The sun must be at a large angle to the sensor's line of sight, with solar radiation passing across the aperture so that the lambertian surface can fill the sensor's field of view with diffusely reflected sunlight. Between calibration cycles the lambertian surface must swing aside, clearing the line of sight, as shown by the double arrow and dashed lines in FIG. 1.

The drawbacks of the calibration procedure similar to the one shown in FIG. 1 are well known. First, the procedure is not ideal for satellites in orbits where the sun is at small, rather than large, angles to the sensor's line of sight. Second, the space required for the lambertian surface to swing in and out of the line of sight takes up a lot of space on the satellite, creating difficulties for satellite designers. Finally, when the sensor is viewing scenes containing regions where the albedo is very close to one (for example high-altitude cloud tops from earth orbit), it is preferable for the detectors to be calibrated using radiances somewhat greater than those coming from the albedo-one regions. However, even using an ideal and diffusely reflective lambertian surface, i.e. one that does not absorb any visible radiation, the procedure shown in FIG. 1 may only produce radiances as great as, and not greater than, those coming from albedo-one regions. Thus, it is likely that the sensor in FIG. 1 is calibrated at radiance levels somewhat less than the brightest radiances measured while in use.

The present invention addresses a solution to the problem of calibrating an imaging sensor disposed in an orbiting satellite using solar radiation. Advantageously, the present invention reduces the angle at which the sun is relative to the sensor's line of sight, reduces the physical space required on the satellite for the lambertian surface to move into the sensor's line of sight, and provides radiance levels that are greater than the brightest radiance levels measured during a typical operation.

SUMMARY OF THE INVENTION

To meet this and other needs, and in view of its purposes, an embodiment of the present invention provides a device for calibrating a sensor using solar radiation. The device includes a sensor configured to measure electromagnetic radiation received through a field of view (FOV) having a normal line of sight and at least two baffles removably insertable across the FOV of the sensor and inclined to the line of sight. Each baffle has first and second opposing surfaces, with the first surface disposed to face the solar radiation and the second surface disposed to face the sensor. One of the first or second surface is configured as a diffused surface, and the other of the first or second surface is configured as a specular surface.

Another embodiment of the present invention provides a system deployed in orbit around earth including an imaging sensor that has a calibration mode and an operational mode. The sensor is configured to receive solar radiation during calibration mode and reflected radiation from the earth during operational mode. The system includes calibration means for calibrating the imaging sensor. The calibration means includes a set of baffles that have at least two plates inclined with respect to the FOV of the imaging sensor. The set of baffles have a calibration position and a stowed position, where the set of baffles in the calibration position intercept solar radiation in the FOV of the imaging sensor, and the set of baffles in the stowed position are moved away from the FOV of the imaging sensor.

In yet another embodiment of the present invention, an imaging sensor disposed in an orbiting satellite is calibrated using solar radiation. First, the set of baffles are moved across the FOV of the imaging sensor, and the baffles are tilted with respect to a normal line of sight of the FOV. The set of baffles then receive the solar radiation in the FOV of the imaging sensor and reflect the solar radiation from the first surface of a baffle onto the second surface of an adjacent baffle. Then, the solar radiation is reflected from the second surface of the adjacent baffle toward the imaging sensor. The imaging sensor is then calibrated using the reflected solar radiation.

BRIEF DESCRIPTION OF THE DRAWING

The invention is best understood from the following detailed description when read in connection with the accompanying drawing. Included in the drawing are the following figures.

DETAILED DESCRIPTION OF THE INVENTION

Figure 2A:
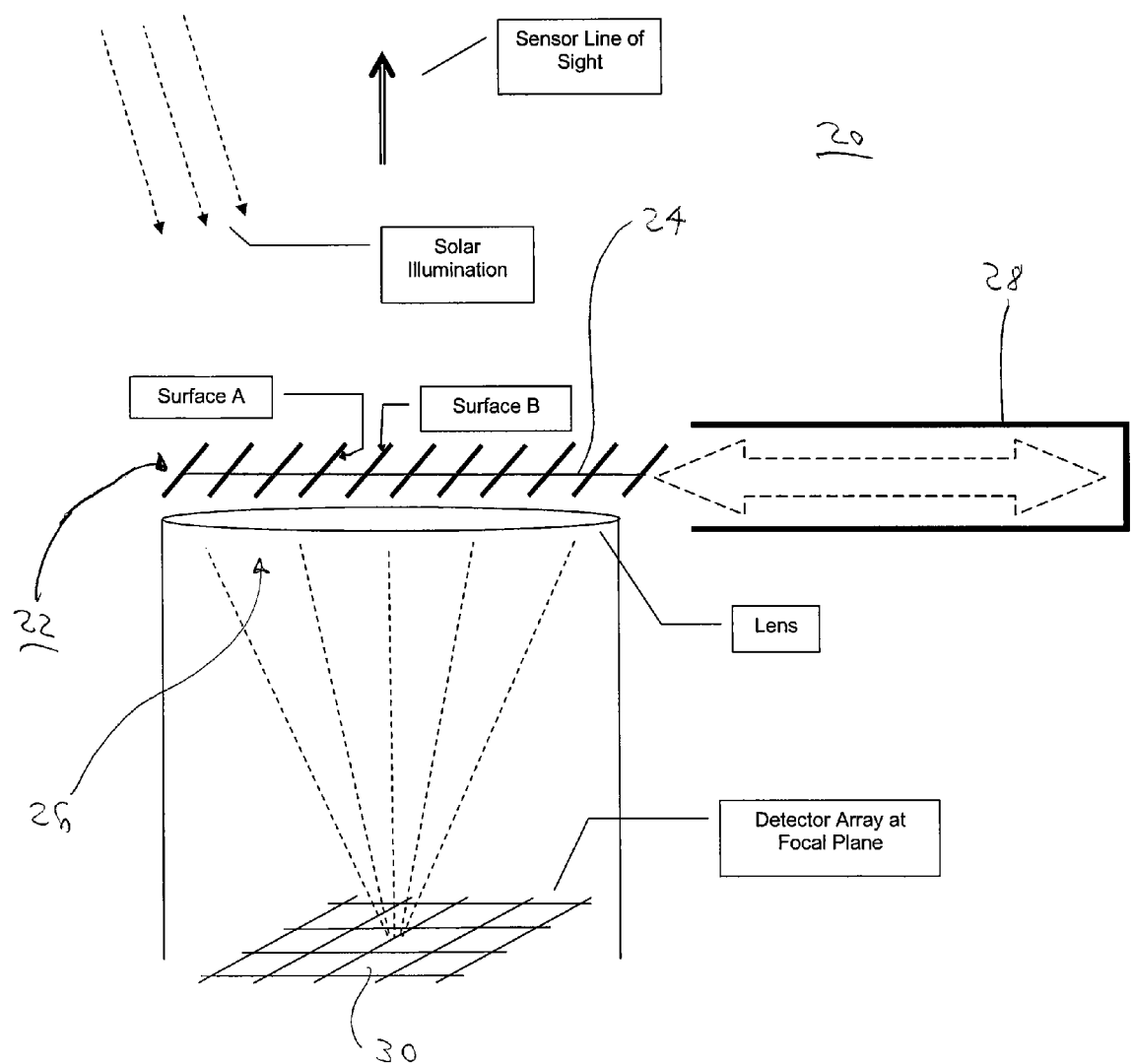
FIG. 2a is a functional block diagram showing a calibration assembly using a set of baffles, in accordance with an embodiment of the present invention.
Figure 2B:
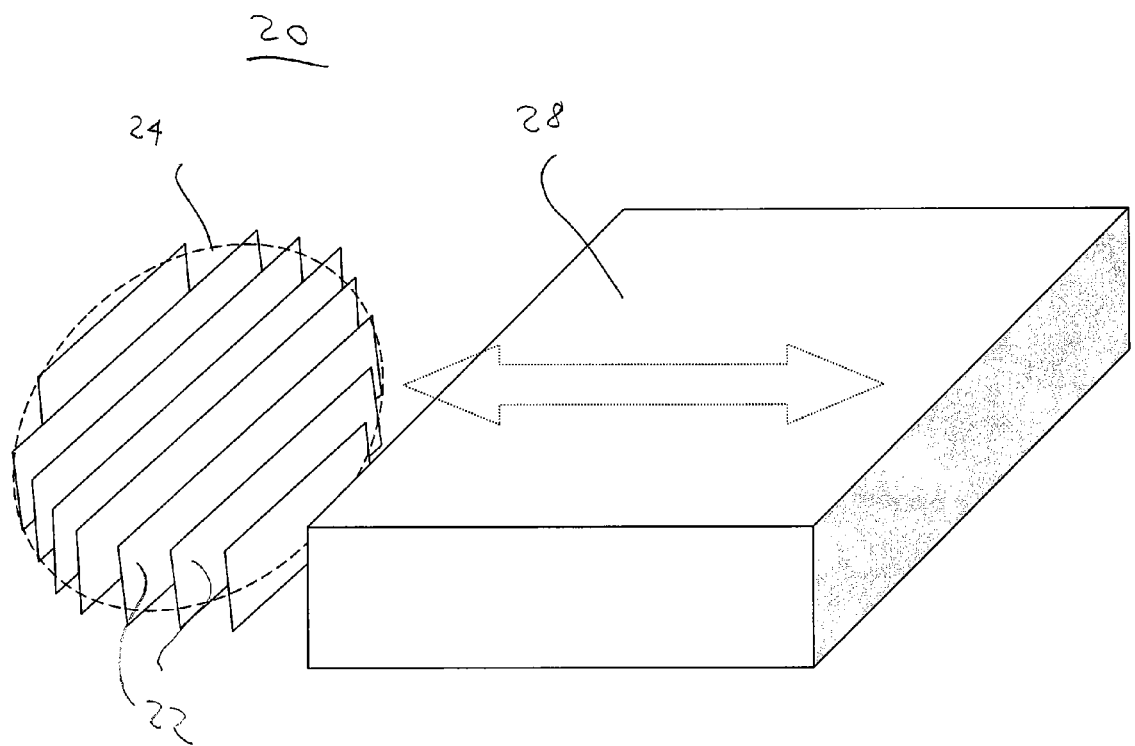
FIG. 2b is a perspective view of a set of baffles held in place by a circular outer loop and stowed away is a storage area, in accordance with an embodiment of the present invention.

FIGS. 2a and 2b show an embodiment of a baffle calibration assembly for an imaging sensor, generally designated as 20. As shown in FIG. 2a, a sequence of closely spaced baffles 22 is placed across the imager's or sensor's input aperture 26. As shown in FIG. 2b, baffles 22 are held in place by outer loop 24. A circular outer loop is shown in FIG. 2b, but any appropriate shape, such as rectangular or hexagonal, may be used. FIGS. 2a and 2b show a small storage device 28 next to the input aperture for holding the baffles when they are not being used for calibration.

Figure 3A:
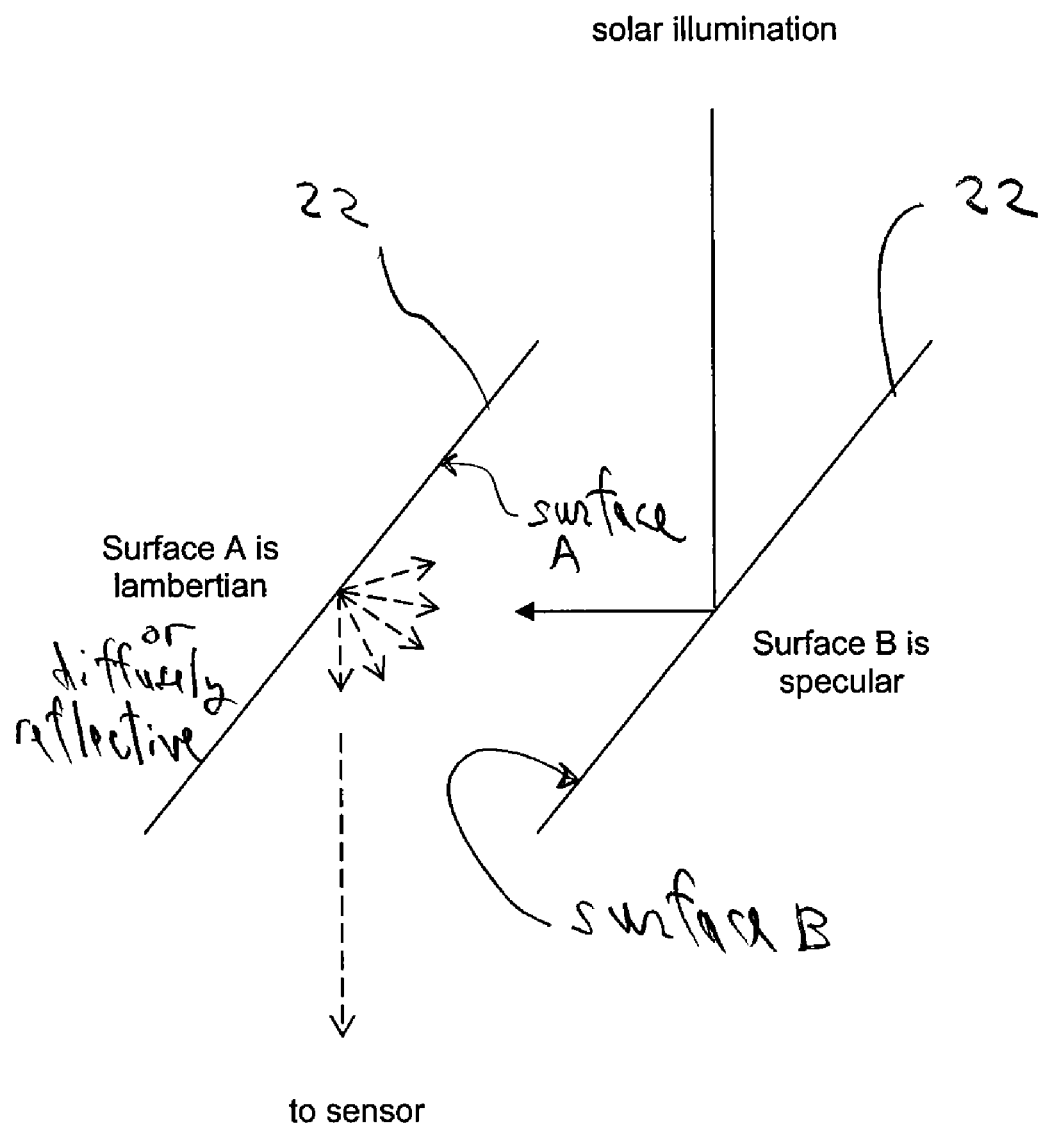
FIG. 3a is a diagram showing solar radiation reflecting from a surface of a first baffle onto the surface of a second baffle, where the surface of the first baffle is specular and the surface of the second baffle is lambertian, in accordance with an embodiment of the present invention.
Figure 3B:
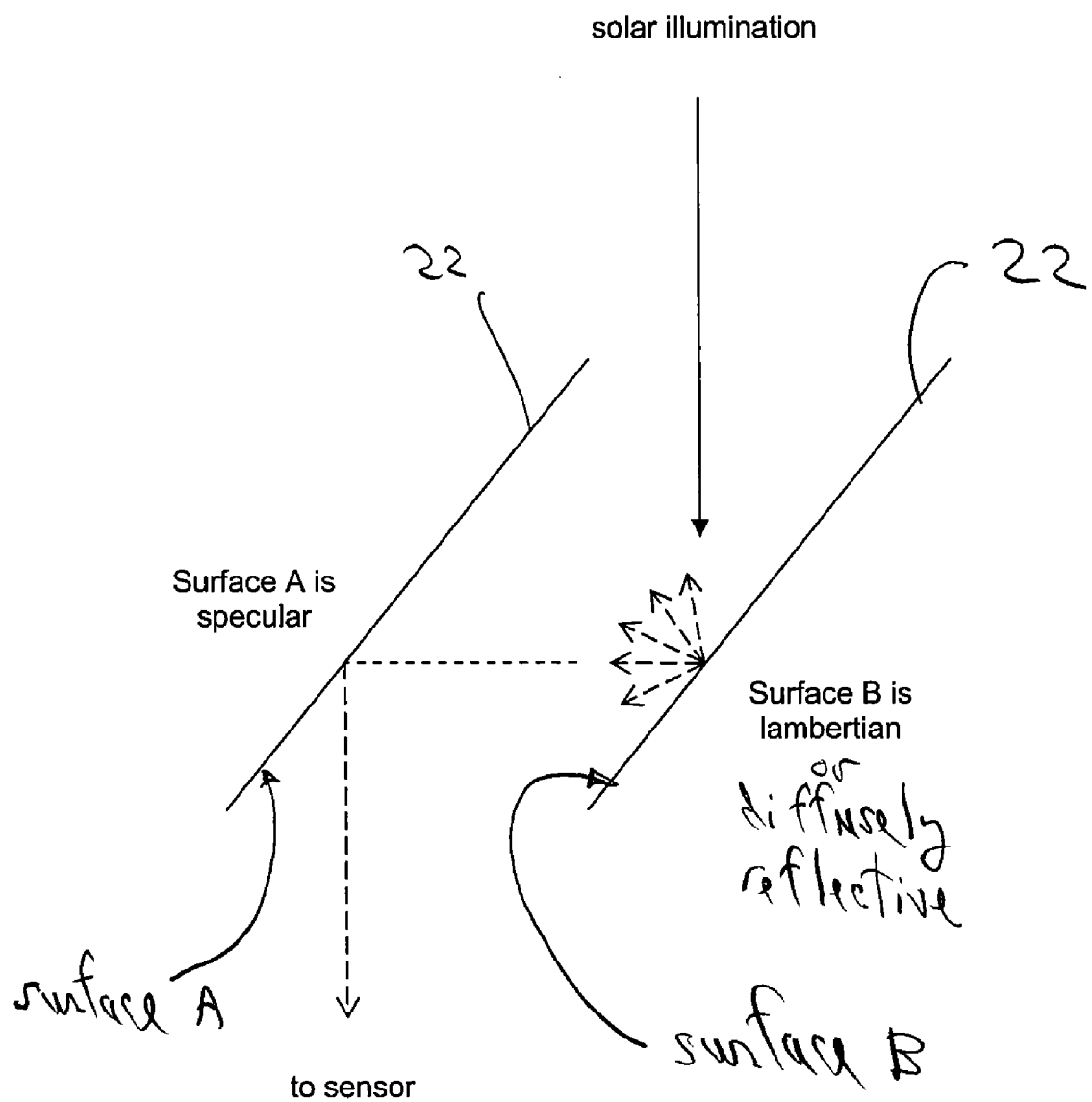
FIG. 3b is a diagram showing solar radiation reflecting from a surface of a first baffle onto the surface of a second baffle, where the surface of the first baffle is lambertian and the surface of the second baffle is specular, in accordance with an embodiment of the present invention.

Each baffle 22 has surface A facing down into detector array 30 and surface B facing outwardly away from array 30. One of these surfaces, either A or B, is lambertian. If not perfectly lambertian, in any case, the surface may be diffusely reflective, with an albedo close to one. FIGS. 3a and 3b show that regardless of which surface is specularly reflective, the sensor detects, and so may be calibrated against, a radiance field produced by a lambertian surface or a diffusely reflective surface. Because the sensor is constructed to view distant scenes, the baffles are in the sensor's near field, which means that any radiance non-uniformities created by the baffles may be averaged into a uniform glow from the viewpoint of detector array 30. FIG. 2a also shows that the baffle calibration assembly is effective, even when the sun is at a relatively small angle with respect to the sensor's line of sight.

Further, the baffle calibration assembly provides a virtual image of the lambertian or diffusely reflective surface formed by the specular surface and produces calibration radiances that are somewhat greater, instead of somewhat less, than the largest radiances measured while the sensor is in use. To show this advantageous result of the present invention, a calibration radiance is calculated below for a specific baffle configuration, one with a lambertian surface albedo equal to 0.9, a specular to 0.9, a specular reflectivity surface equal to 0.95, and the sun directly in the sensor's line of sight (The angle between the solar radiation and the sensor line of sight is 0 degrees).

Figure 4A:
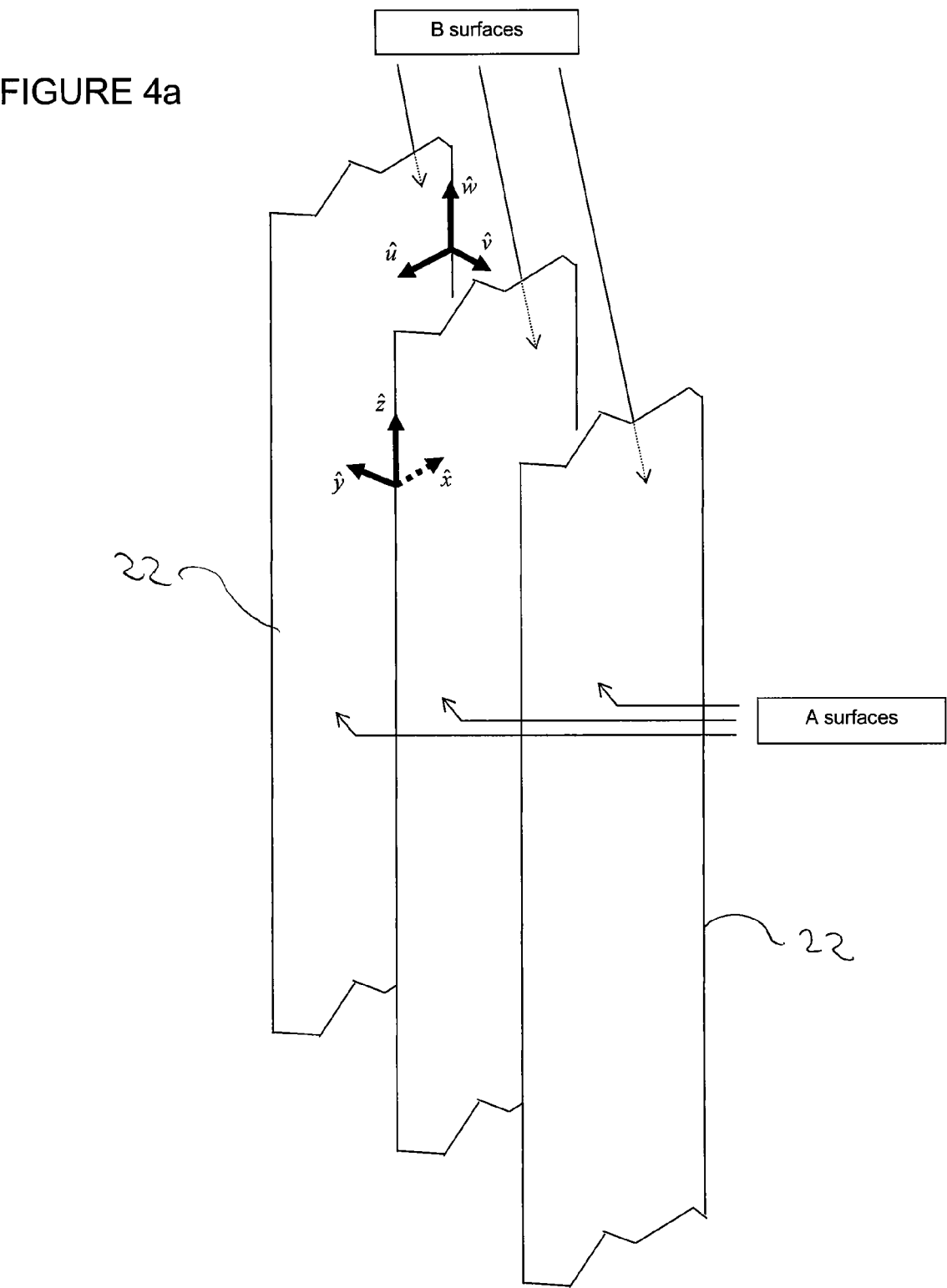
FIGS. 4a and 4b are coordinate systems defined for the surfaces of each baffle.
Figure 4B:
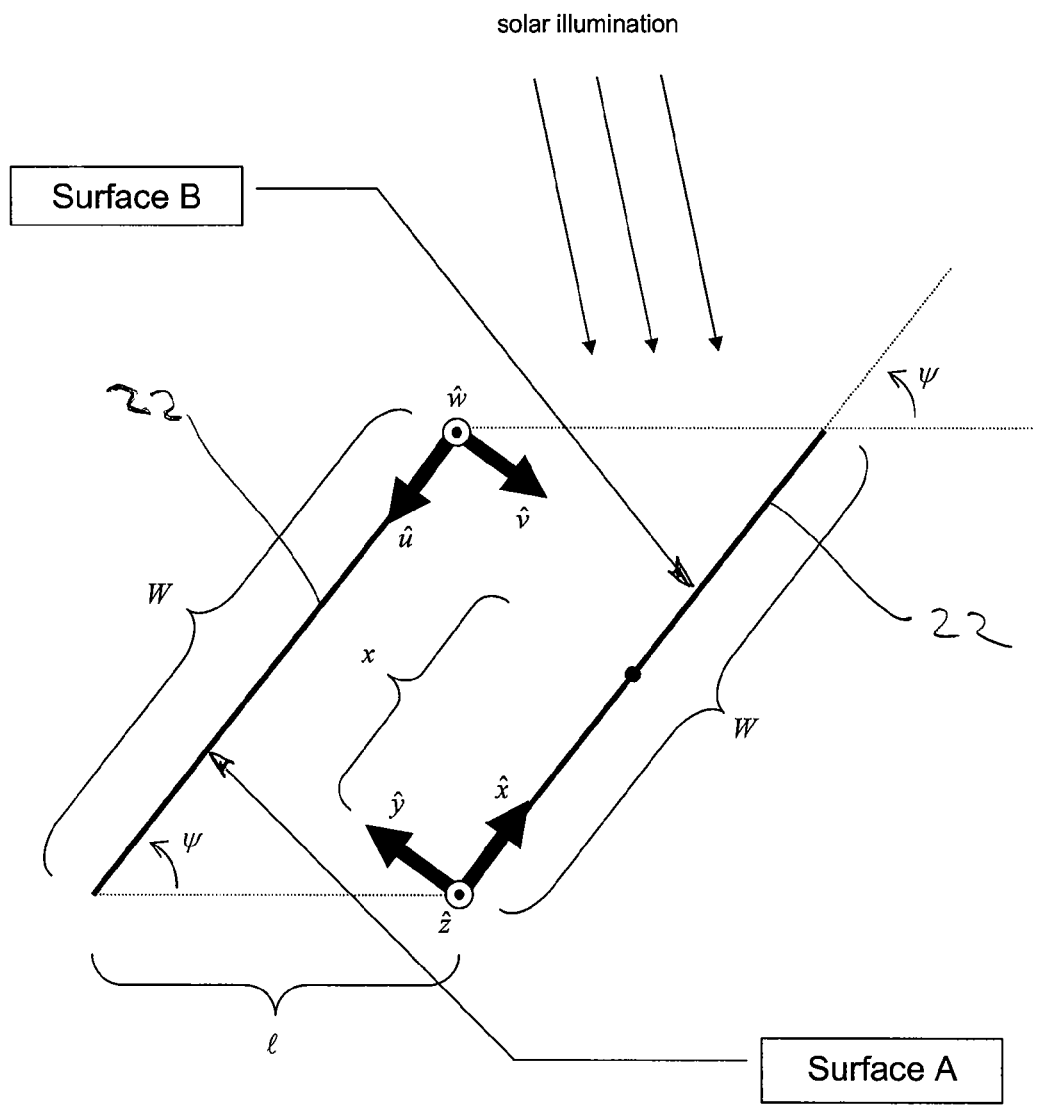
Figure 4C:
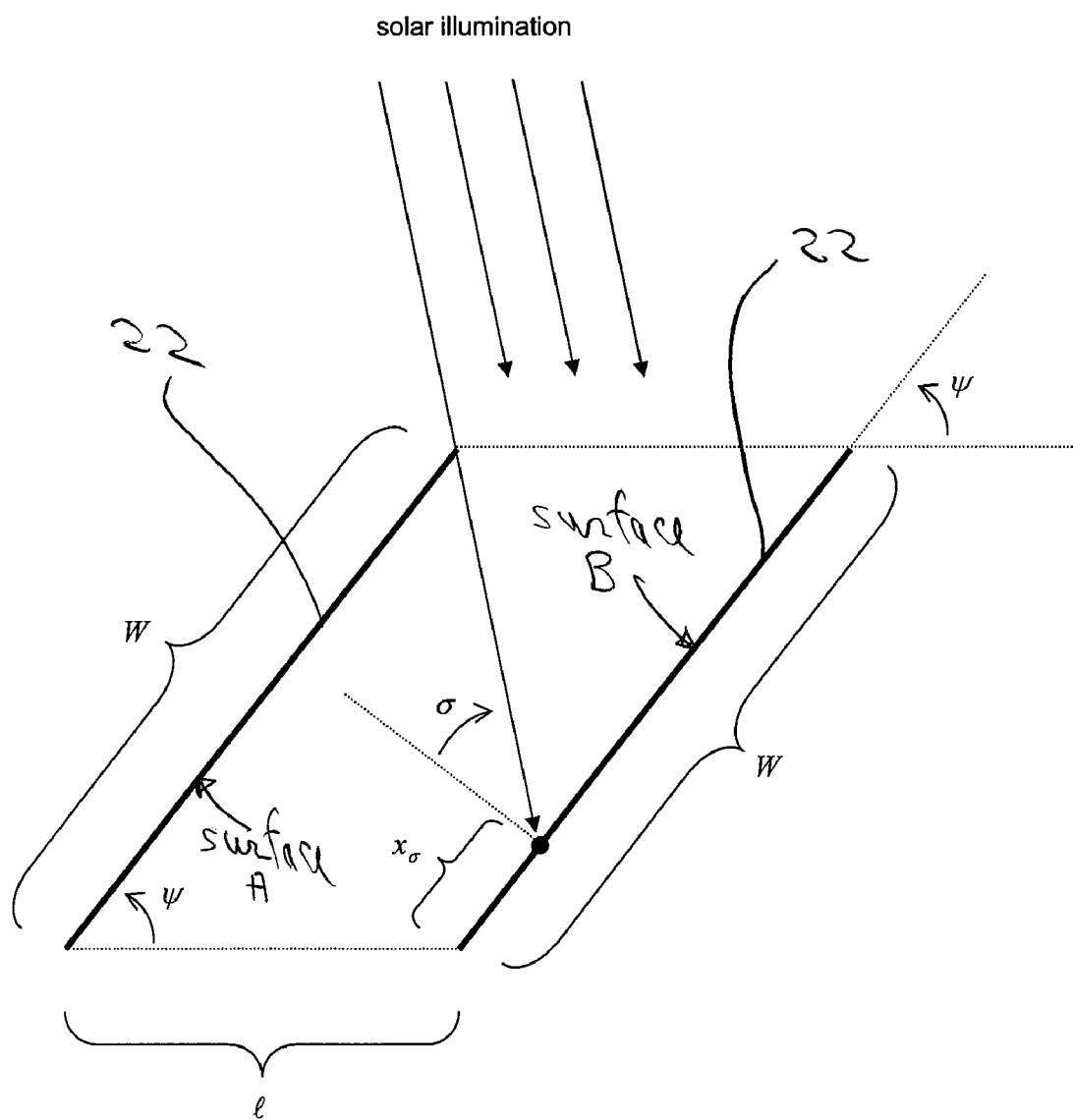
FIG. 4c includes a separation distance between baffles.

It is assumed that the calibrating baffles are thin and close together so that they may be approximated as being long compared to their width, as shown in FIG. 4a. FIGS. 4a and 4b show two coordinate systems specified for the baffles: a u, v, w Cartesian coordinate system on surface A and an x, y, z Cartesian coordinate system on surface B. FIGS. 4b and 4c show that each baffle has a width of W with the edges of surfaces A and B separated by a distance. In this example, surfaces A and B are inclined at the same angle $\psi$. It will be noted, however, that the calibration baffles are also effective if each baffle is wedged, forming surfaces A and B at different angles with respect to each other, so long as there is room or opening for sunshine to pass into the baffles.

Figure 4D:
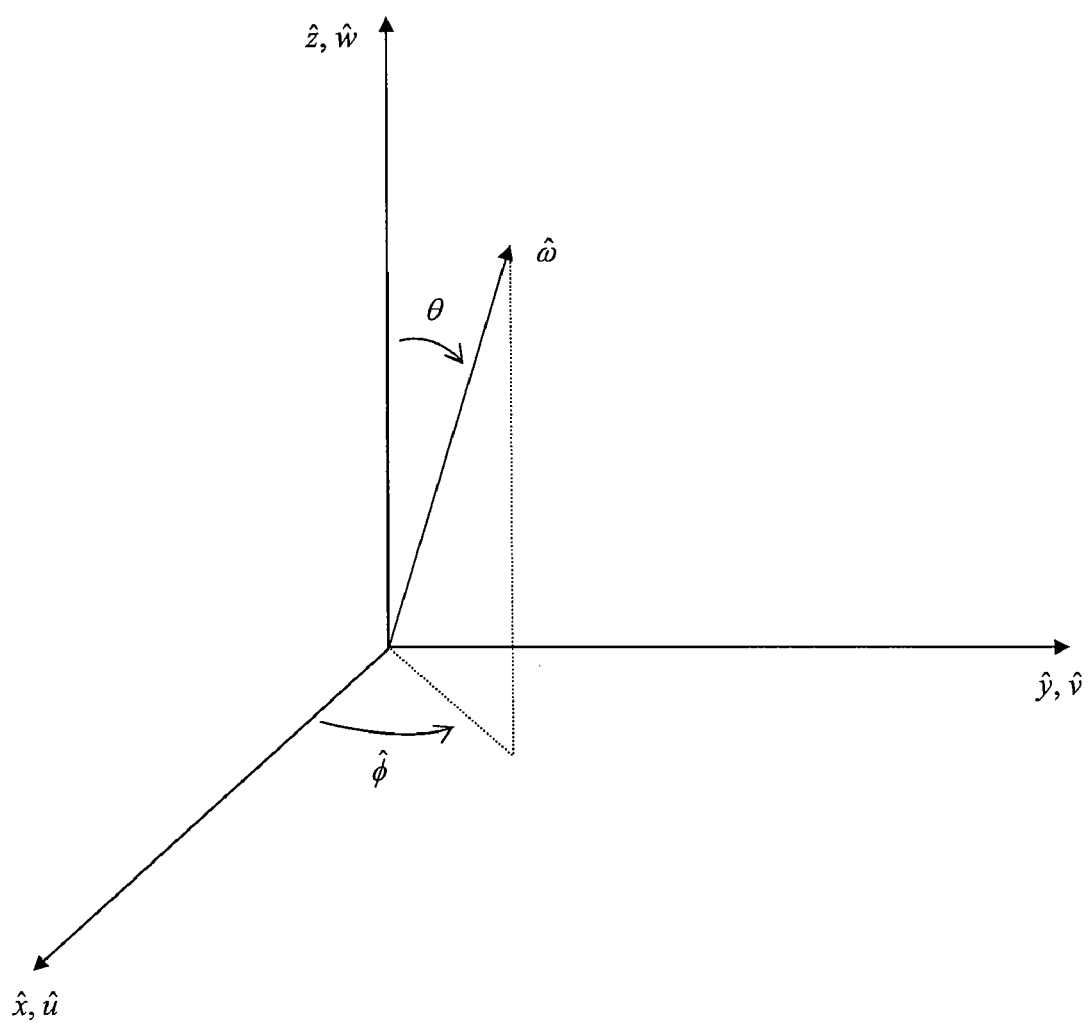
FIG. 4d depicts polar and azimuthal angles associated with the coordinate systems defined for the surfaces of each baffle.

FIG. 4d defines standard polar and azimuthal angles $\theta$, $\phi$ associated with the x, y, z and u, v, w coordinate systems. Unit vectors $$\hat{\omega}_{\theta\phi}^{(\hat{x},\hat{y},\hat{z})} = \hat{x} \sin\theta \cos\phi + \hat{y} \sin\theta \sin\phi + \hat{z} \cos\theta \quad (1a)$$

and $$\hat{\omega}_{\theta\phi}^{(\hat{u},\hat{v},\hat{w})} = \hat{u} \sin\theta \cos\phi + \hat{v} \sin\theta \sin\phi + \hat{w} \cos\theta \quad (1b)$$

are defined with respect to the x, y, z and u, v, w coordinate systems. At any point on surface B, unit vector $\hat{\omega}_{\theta\phi}^{(\hat{x},\hat{y},\hat{z})}$ specifies a unique direction in space. Similarly, at any point on surface A, unit vector $\hat{\omega}_{\theta\phi}^{(\hat{x},\hat{y},\hat{z})}$ specifies a unique direction in space.

Having set up two generalized coordinate systems that may be used for different calibration-baffle configurations, a calibration-baffle set-up where surface A is specular and surface B is lambertian will now be analyzed. $E_B$ is defined as the spectral radiant exitance (in optical power per unit surface area per unit wavelength unit wavelength interval) leaving surface B. Since surface B is lambertian, the spectral radiance (in optical power per unit cross-sectional area per unit solid angle per unit wavelength interval) is $$L_B = \frac{E_B}{\pi} \quad (2a)$$

and the spectral irradiance (in optical power per unit surface area per unit wavelength interval) is $I_B$ so that $$E_B = \alpha I_B \quad (2b)$$

where $\alpha$ is the albedo of surface B for the wavelength at which the spectral exitance and spectral irradiance are measured.

FIG. 4c shows how surface A shadows surface B from the sun. The unit vector pointing toward the center of the sun is defined to be $\hat{\omega}_{sun}$ and according to equation (1a) can be written as $$\hat{\omega}_{sun} = \hat{x} \sin\theta_{sun} \cos\phi_{sun} + \hat{y} \sin\theta_{sun} \sin\phi_{sun} + \hat{z} \cos\theta_{sun} \quad (3a)$$

where $\theta_{sun}$, $\phi_{sun}$ are respectively the polar and azimuthal angles in the x, y, z coordinate system of the sun's position with respect to surface B. The formula for the x coordinate of the shadow edge on surface B, $x_\sigma$, is $$x_\sigma = W - l \cos\psi - l \sin\psi \tan\sigma \quad (3b)$$

where angle σ is given by $$\sigma = \frac{\pi}{2} - \phi_{sun}. \tag{3c}$$

The Heaviside step function is defined by $$H(\xi) = \begin{cases} 1 \text{ for } \xi > 0 \\ 0 \text{ for } \xi \leq 0 \end{cases}, \tag{3d}$$

which means the solar irradiance on surface B may be written as $$I_B^{(sun)} = KH(x - x_\sigma) \tag{3e}$$

where $$K = L_{sun}\Delta\Omega_{sun}(\hat{\omega}_{sun} \cdot \hat{y}) = L_{sun}\Delta\Omega_{sun}\sin\theta_{sun}\sin\phi_{sun}. \tag{3f}$$

Here, $L_{sun}$ is the sun's spectral radiance in the wavelength band of interest, $\Delta\Omega_{sun}$ is the solid angle subtended by the sun's disk at the position of the sensor, and "•" represents the vector dot product.

According to equation (3e), the solar spectral irradiance at any point of surface B depends only on the x coordinate of that point. Symmetry requires this to be true not only for the solar spectral irradiance $I_B^{(sun)}$ but also for the total spectral irradiance $I_B$. Hence, it is true that $I_B^{(sun)} = I_B^{(sun)}(x)$ and also that $$I_B = I_B(x). \tag{4a}$$

Combining equations (2a,b) with equation (4a), the same is true of the total spectral exitance and radiance at any point on surface B—both depend only on the x coordinate of that point:

$$E_B = E_B(x) \tag{4b}$$

and $$L_B = L_B(x). \tag{4c}$$

Since the z coordinates of points on surface B are irrelevant, all points on surface B having the same x value are equivalent. Consequently, referring to "point x" on surface B, or "the x value of a point" on surface B is not ambiguous, i.e. it does not overlook the three-dimensional nature of the baffles or the two-dimensional nature of the surface.

Figure 5A:
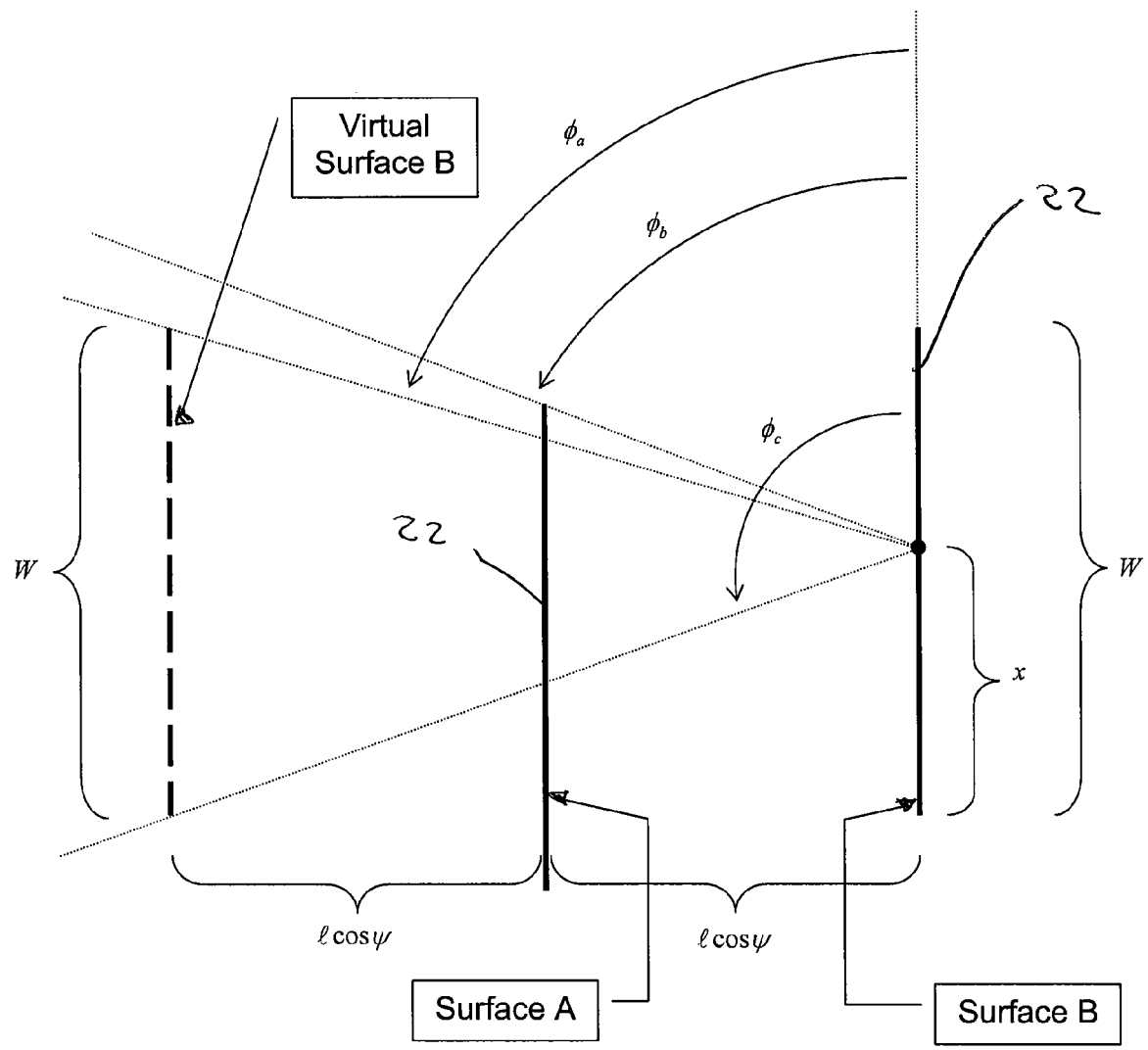
FIGS. 5a and 5b show virtual surfaces formed by reflecting sunlight off real surfaces formed by the baffles.
Figure 5B:
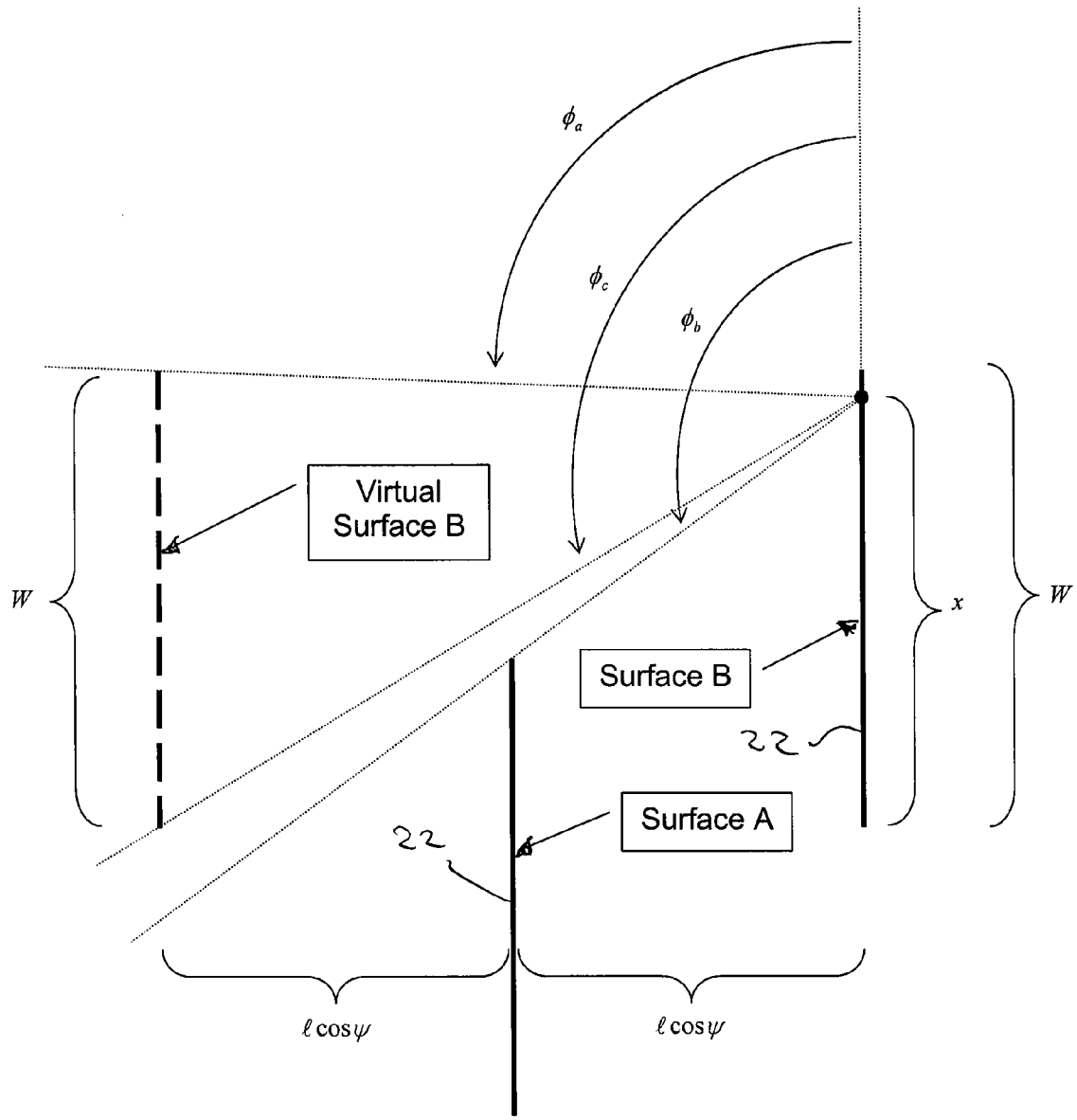

FIGS. 5a and 5b use the edges of surface A, and the edges of the virtual image of surface B formed by specular reflection off surface A, to define three angles $\phi_a$, $\phi_b$, $\phi_c$ for any point x on surface B. The formulas for angles $\phi_a$, $\phi_b$, $\phi_c$ are $$\phi_a(x) = \frac{\pi}{2} - \tan^{-1}\left(\frac{W-x}{2l\sin\psi}\right) \tag{5a}$$

$$\phi_b(x) = \frac{\pi}{2} + \tan^{-1}\left(\frac{x - W + l\cos\psi}{l\sin\psi}\right) \tag{5b}$$

and $$\phi_c(x) = \frac{\pi}{2} + \tan^{-1}\left(\frac{x}{2l\sin\psi}\right). \tag{5c}$$

Figure 6:
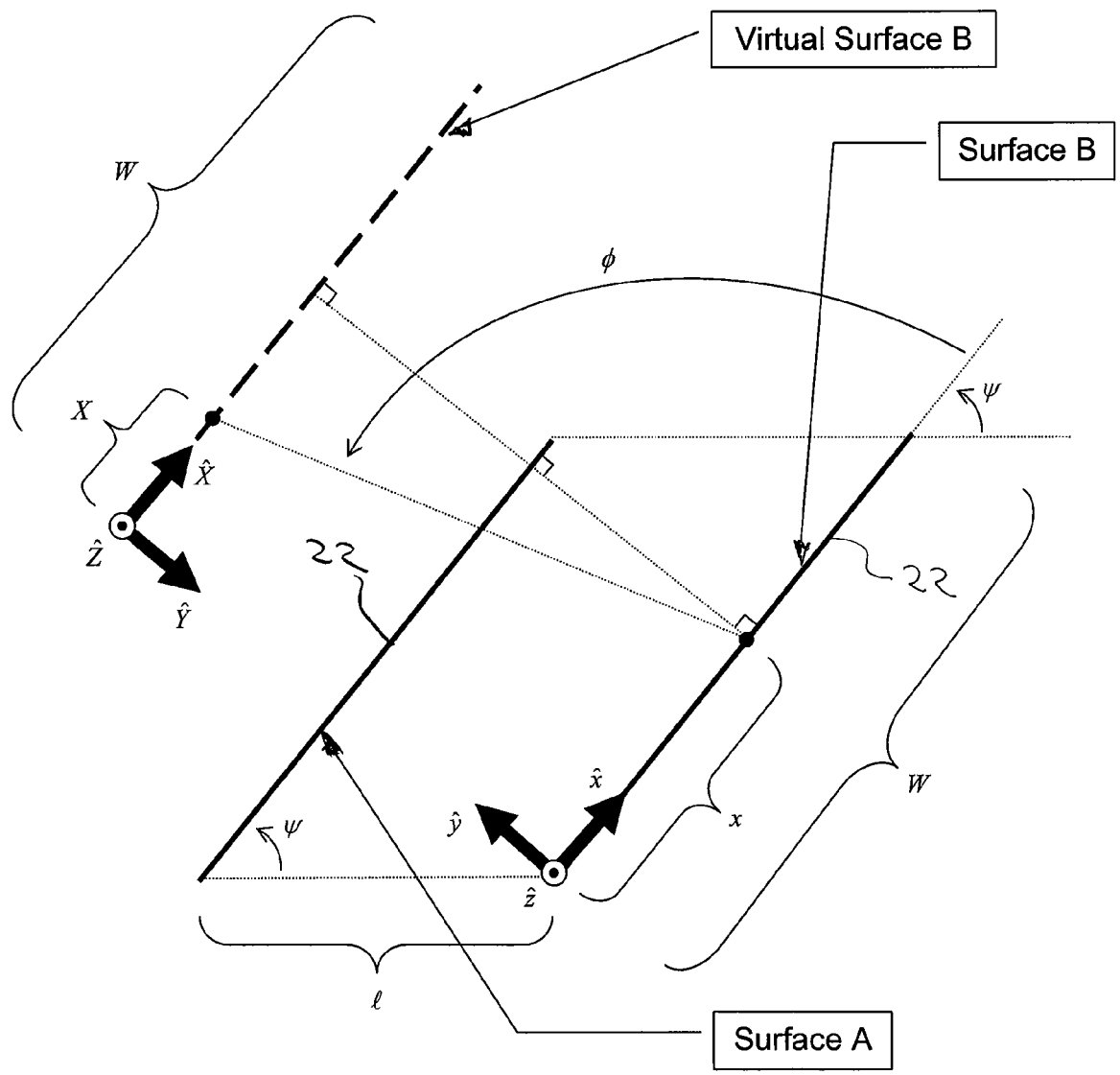
FIG. 6 shows another virtual image formed by reflection off one surface of a baffle.

FIG. 6 shows the relationship of the azimuthal angle φ to the virtual image of surface B created by specular reflection off surface A. An X, Y, Z coordinate system is constructed for virtual surface B that is the mirror image of the x, y, z coordinate system of surface B. The formula connecting coordinate x on surface B, coordinate X on virtual surface B, and angle φ is which may also be written $$\phi = \frac{\pi}{2} + \tan^{-1}\left(\frac{(W-X)-(W-x)}{2l\sin\psi}\right)\tan\left(\phi - \frac{\pi}{2}\right) = \frac{x-X}{2l\sin\psi},$$

and then simplified to $$X = x + 2l(\sin\psi)\cot\phi \tag{6a}$$

An integral equation for $I_B(x)$, the total irradiance at any point (x,0,z), (x,0,z), may be constructed by taking the coordinates of points on virtual surface B into account. As already described above, $I_B$ cannot depend on the z coordinate of surface B, so nothing is lost by assuming that z=0. As a start, $$\Delta\lambda\Delta x\Delta z[I_B(x)] = \Delta\lambda\Delta x\Delta z I_B^{(sun)}(x) + \tag{6b}$$

$$\int_0^\pi d\theta\sin\theta \int_{\phi_{sm}(x)}^{\phi_{lg}(x)} d\phi\left\{\left[(\hat{\omega}_{\theta\phi}^{(\hat{x},\hat{y},\hat{z})} \cdot \hat{y})\Delta x\Delta z\right]L_{BV}(x + 2l\sin\psi\cot\phi)\Delta\lambda\right\}.$$

In equation (6b), Δx Δz is an element of area on surface B and $\hat{\omega}_{\theta\phi}^{(\hat{x},\hat{y},\hat{z})}$ is a dimensionless unit vector pointing from point (x,0,0) on surface B (recall that z=0) to a position on the virtual surface B specified by polar angle θ and azimuthal angle φ. Function $L_{BV}$ is the spectral radiance coming from virtual surface B as it reaches point (x,0,0) and Δλ is the wavelength interval over which the optical power is specified. By symmetry, $L_{BV}$ may only depend on X, which is why it has only the one argument specified in equation (6b). The radiance from all values of Z, however, may reach point (x,0,0). Consequently, the integral over all solid angle elements $$d\Omega = (\sin\theta)d\theta d\phi \tag{6c}$$

is added in equation (6b) to the solar irradiance on surface B, $I_B^{(sun)}(x)$, which point back to positions (X,0,Z) on virtual surface B. Hence, the double integral in equation (6b) is over dθ between 0, π and over dφ between $\phi_{sm}(x)$, $\phi_{lg}(x)$. Here, $\phi_{sm}(x)$ is the smallest value of φ at point (x,0,0) that points back to virtual surface B, and $\phi_{lg}(x)$ is the largest value of φ that points back to virtual surface B. Inside the double integral, the quantity enclosed by square brackets [ ] is the area Δx Δz at point (x,0,0) which has been projected perpendicularly to the θ, φ rays coming from virtual surface B. Therefore $$[(\hat{\omega}_{\theta\phi}^{(\hat{x},\hat{y},\hat{z})} \cdot \hat{y})\Delta x\Delta z]$$

inside the double integral is the cross-sectional area for the radiance $L_{BV}$ along the ray going from point (X,0,Z) to point (x,0,0). From equations (2a,b) above, $$L_B = \frac{\alpha I_B}{\pi} \tag{6d}$$

If $\rho$ is the specular reflectivity of surface A, then $$L_{BV} = \rho L_B = \frac{\rho \alpha I_B}{\pi} \qquad (6e)$$

Equations (4a) and (4c) show that $I_B$ and $L_B$ depend only on x, and as shown above, $L_{BV}$ depends only on X. Hence, inside the double integral in equation (6b), it is necessary to evaluate $L_{BV}$ at the value of X corresponding to the $\theta$, $\phi$ angle pair. Fortunately, as shown by equation (6a), the value of X depends only on $\phi$, so $L_{BV}$ may be written as a function only of $\phi$ by using $$x + 2l \sin \psi \cot \phi$$

for its argument inside the double integral.

Simplifying equation (6b), the $\Delta\lambda \, \Delta x \, \Delta z$ product cancels out on both sides of the equation, and formula (1a) shows that $$\hat{\omega}_{\theta\phi}^{(\bar{x},\bar{y},\bar{z})} \cdot \hat{y} = \sin \theta \sin \phi \qquad (7a)$$

which may be substituted into (6b) to get $$I_B(x) = I_B^{(sun)}(x) + \int_0^\pi d\theta \sin^2 \theta \int_{\phi_{sm}(x)}^{\phi_{lg}(x)} d\phi (\sin\phi) L_{BV}(V_\phi + x) \qquad (7b)$$

where $$V_{100} = 2l \sin \psi \cot \phi \qquad (7c)$$

The integral over d$\theta$ may be in closed form, $$\int_0^\pi (\sin^2 \theta) d\theta = \frac{\pi}{2} \qquad (7d)$$

which, together with equations (3e) and (6e) shows that $$I_B(x) = K H(x - x_\sigma) + \frac{\alpha\rho}{2} \int_{\phi_{sm}(x)}^{\phi_{lg}(x)} (\sin\phi) I_B(V_\phi + x) d\phi \qquad (7e)$$

Finally, functions $\phi_{sm}(x)$ and $\phi_{lg}(x)$ may be defined as follows: From FIGS. 5a and 5b, $$\phi_{sm}(x) = \phi_a(x) \text{ and } \phi_{lg}(x) = \phi_c(x) \text{ when } \phi_b(x) \leq \phi_a(x) \qquad (7f)$$

and $$\phi_{sm}(x) = \phi_b(x) \text{ and } \phi_{lg}(x) = \phi_c(x) \text{ when } \phi_a(x) < \phi_b(x) \leq \phi_c(x). \qquad (7g)$$

When $\phi_b(x) > \phi_c(x)$, the following may be defined:

$$\phi_{sm}(x) = \phi_{lg}(x) = \frac{\pi}{2} \qquad (7h)$$

Equation (7h) ensures that the integral in (7e) is zero, because for $\phi_b(x) > \phi_c(x)$, no radiation from virtual surface B reaches surface B, i.e. surface A cannot reflect back to surface B any of the radiation leaving surface B, when $\phi_b(x) > \phi_c(x)$.

Equation (7e) may be solved using the method of successive iterations described on pages 109-110 of Radiation Heat Transfer by E. M. Sparrow and C. D. Cess (Augmented edition, Hemisphere Publishing Company, New York, 1978).

Figure 1:
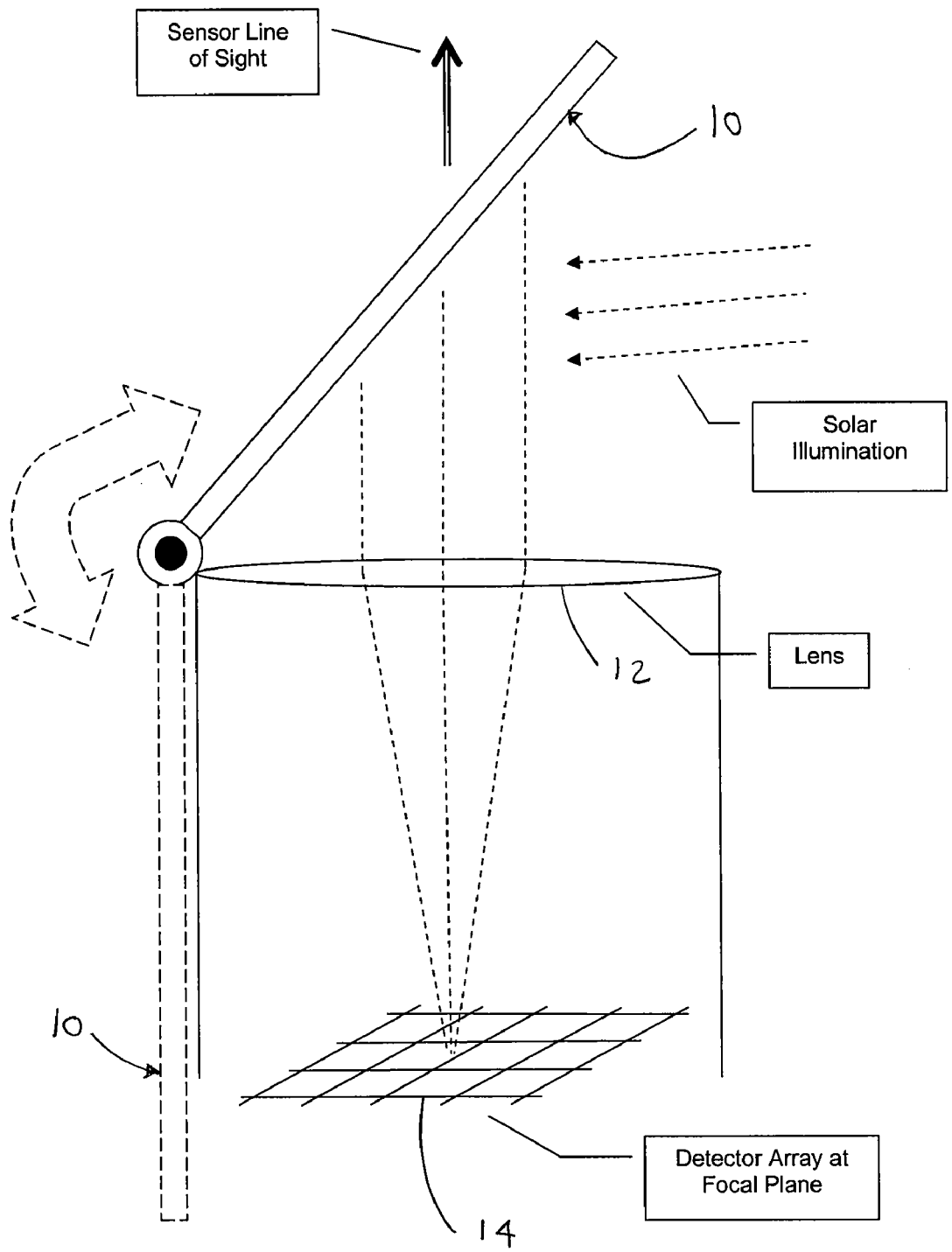
FIG. 1 shows a prior art assembly for calibrating an imaging sensor using solar radiation.

To compare performance of the calibration baffles to the single calibration surface shown in FIG. 1, it is assumed that both the single calibration surface and the B surfaces of the calibration baffles have the same albedo $\alpha$. Then, the baffle radiances may be normalized by $$L_N = \frac{\alpha K}{\pi}, \qquad (8a)$$

the radiance leaving the single lambertian surface in FIG. 1 when the sun illuminates it at the same angle that it illuminates the B surfaces of the calibration baffles. Note that for the single lambertian surface, all the rays entering the sensor in FIG. 1 direct the same $L_N$ radiance into the sensor. For the calibration baffles, on the other hand, the rays have radiance values $L_{cal}$ that depend on the x coordinate from which they leave surface B, before they reflect off surface A and enter the sensor. Thus, for the calibration baffles $$L_{cal}(x) = \frac{\rho \alpha I_B(x)}{\pi} \qquad (8b)$$

where $I_B(x)$ satisfies equation (7d), above. Hence, the normalized radiance is also a function of x, $$L_{cal}^{(N)}(x) = \frac{\rho \alpha I_B(x)}{\pi L_N} = \frac{\rho I_B(x)}{K} \qquad (8c)$$

which may be calculated by solving for $I_B(x)$ and then multiplying by $\rho/K$. Setting $$W = 1 \text{ cm}, l = \frac{1}{\sqrt{2}} \text{cm, and} \qquad (8d)$$

$$\psi = \frac{\pi}{4}, \phi_{sun} = \frac{\pi}{4}, \theta_{sun} = \frac{\pi}{2} \qquad (8e)$$

and, for a sensor orbiting the earth, $$K = \frac{\Delta \Omega_{sun} L_{sun}}{\sqrt{2}} \cong 1.4 \times 10^{10} \text{ erg/sec/cm}^3. \qquad (8f)$$

Figure 7:
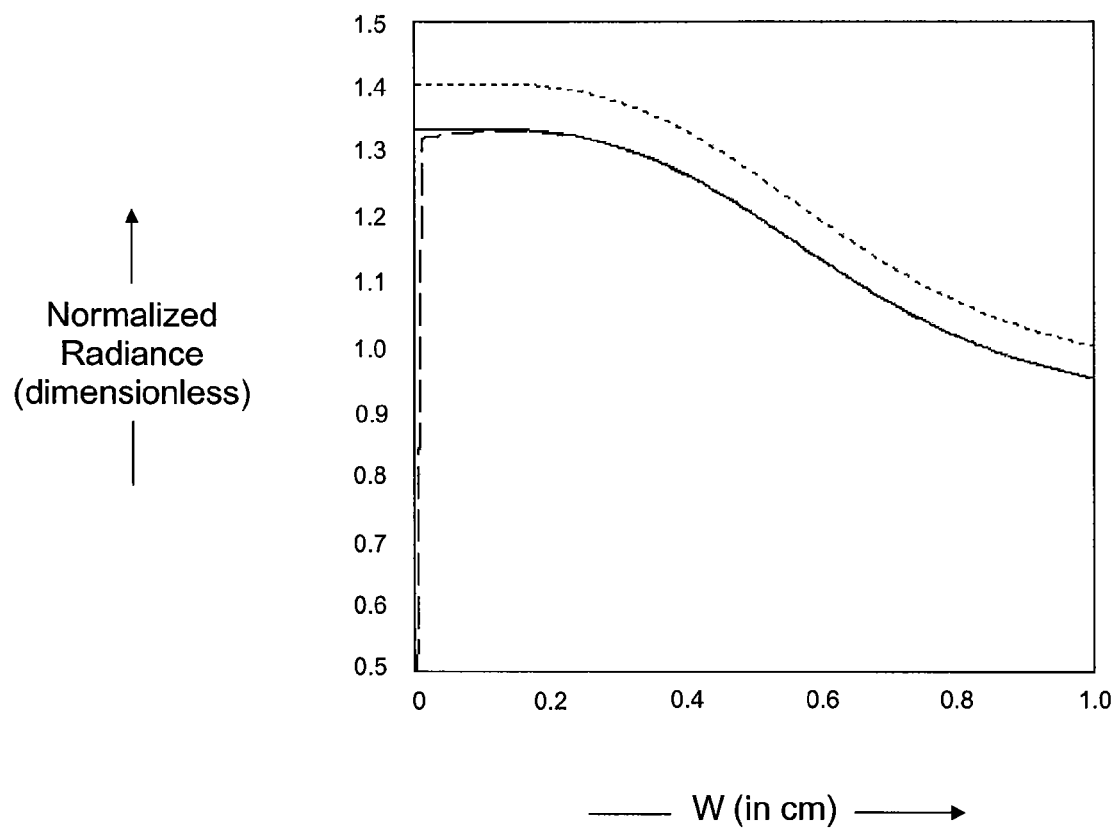
FIG. 7 is a plot of normalized radiance versus the width of the baffles, shown in FIGS. 2a and 2b, when a first surface is specularly reflective and a second surface is lambertian, in accordance with an embodiment of the present invention.

From equations (3b) and (3c), it may be seen that $x_\sigma = 0$ because, in the ideal setup specified by equations (8d) and (8e), surface A does not cast a shadow on surface B. Solving for $I_B(x)$ from equation (7e) with $$\alpha = 0.9 \text{ and } \rho = 0.95, \qquad (8g)$$

and multiplying by $\rho/K$, $L_{cal}^{(N)}(x)$ is produced, which is represented by the solid curve shown in FIG. 7.

Experimenting with the value of $\rho$ shows that when $\rho = 1$ the entire $L_{cal}^{(N)}(x)$ curve created by a perfectly reflective specular surface is greater than or equal to $L_{cal}^{(N)} = 1$, as shown by the dotted curve in FIG. 7. A more realistic value for a high-performance specular surface is $\rho = 0.95$, because some shadowing of surface B by surface A may exist due to the finite thickness of the baffles. Hence, the value of l may be adjusted slightly, using $$l = \frac{0.995}{\sqrt{2}} \text{cm} \tag{8h}$$

This produces the dashed curve for $L_{cal}^{(N)}(x)$ in FIG. 7. It is virtually identical to the solid curve except near the shadow at very small values of x. Since the baffles are in the near field of the sensor, i.e. they are out of focus, the sensor observes a uniform glow during calibration, just as if it were looking at the single calibration surface in FIG. 1. The effective normalized and uniform radiance of this glow is calculated by averaging over the solid and dashed solution curves in FIG. 7 to get $$\frac{1}{W}\int_0^W L_{cal}^{(N)}(x)dx \cong \begin{cases} 1.175 & \text{for the solid curve} \\ 1.169 & \text{for the dashed curve} \end{cases} \tag{8i}$$

The value of the integral is much the same for both the shaded and unshaded models, showing that introducing a small amount of shadow into the idealized system does not materially affect the result. The integral is also clearly greater than one. Therefore, the virtual image of surface B created by surface A produces calibration radiances somewhat greater, instead of somewhat less, than the largest radiances measured while the sensor is in use.

The above derivation assumed that the A surfaces are specularly reflective and the B surfaces are lambertian. Reversing this assumption for the case analyzed above, using equations (8d-g), it may be shown that, when the B surfaces are specularly reflective and the A surfaces are lambertian, the virtual image of surface A formed by the mirror of surface B plays the same role at the same relative location as the virtual image of surface B in the mirror of surface A did previously. Since once again $x_o = 0$, it may be written that $$I_A(u)|_{\substack{specular B \\ lambertian A}} = \rho I_B(u)|_{\substack{specular A \\ lambertian B}}.$$

The factor of $\rho$ comes from the solar radiance being diminished by $1/\rho$ after it reflects specularly off surface B. Here, $$I_A(u)|_{\substack{specular B \\ lambertian A}}$$

is the irradiance of the diffusely reflective surface A when surface B is specular, and $$I_A(x)|_{\substack{specular A \\ lambertian B}}$$

is the irradiance of the diffusely reflective surface B when surface A is specular. The x coordinate is associated with the $\hat{x}$ axis of the x, y, z coordinate system shown in FIGS. 4a and 4b and takes on values between 0 and W on surface B. Similarly, the u coordinate is associated with the $\hat{u}$ axis of the u, v, w coordinate system shown in FIGS. 4a and 4b and takes on values between 0 and W on surface A. Note that the direction in which u increases is opposite to the direction in which x increases, which is the property required for the relationship $$I_A(u)|_{\substack{specular B \\ lambertian A}} = \rho I_B(u)|_{\substack{specular A \\ lambertian B}}$$

to make sense. Therefore, the sensor observes a normalized and uniform radiance equal to $$\frac{1}{W}\int_0^W L_{cal}^{(N)}(u)du \cong 1.17 \tag{9a}$$

where $$L_{cal}^{(N)}(u) = \frac{\alpha}{\pi L_N} I_A(u)\bigg|_{\substack{specular B \\ lambertian A}} = \frac{\rho}{K} I_B(u)\bigg|_{\substack{specular A \\ lambertian B}} \tag{9b}$$

Thus, the calibration baffles direct more diffusely reflected sunlight into the sensor than does the single calibration surface in FIG. 1. In general, there is no significant difference in performance when the B surfaces, instead of the A surfaces, are specularly reflective.

If less solar illumination is required to calibrate the sensor, both surface A and surface B may be made diffusely reflective and lambertian. In this type of baffle assembly $\alpha_A$ is the albedo of surface A and $\alpha_B$ is the albedo of surface B. The same type of analysis under the same set of assumptions used to derive equation (7e) above, when applied to this new type of baffle assembly, results in a pair of coupled integral equations for $I_A(u)$, the total irradiance on surface A as a function of coordinate u, and $I_B(x)$, the total irradiance on surface B as a function of coordinate of coordinate x. These equations are $$I_A(u) = \frac{\alpha_B}{2}\int_{\phi_{min}(u)}^{\phi_{max}(u)}(\sin\phi)I_B(\Lambda_\phi - u)d\phi \tag{10a}$$

and $$I_B(x) = K\ H(x - x_\sigma) + \frac{\alpha_A}{2}\int_{\phi_{min}(x)}^{\phi_{max}(x)}(\sin\phi)I_A(\Lambda_\phi - x)d\phi \tag{10b}$$

where $$\phi_{min}(\xi) = \begin{cases} \tan^{-1}\left(\dfrac{l\sin\psi}{W - l\cos\psi - \xi}\right) & \text{for } \xi \leq W - l\cos\psi \\ \dfrac{\pi}{2} + \tan^{-1}\left(\dfrac{\xi + l\cos\psi - W}{l\sin\psi}\right) & \text{for } \xi > W - l\cos\psi \end{cases} \tag{10c}$$

and $$\phi_{max}(\xi) = \frac{\pi}{2} + \tan^{-1}\left(\frac{\xi + l\cos\psi}{l\sin\psi}\right) \tag{10d}$$

with $$\Lambda_\phi = W - l\cos\psi - l\sin\psi\cot\phi. \tag{10e}$$

Having solved for $I_A(u)$ and $I_B(x)$, only the $I_A(u)$ values produce radiances that directly enter the sensor. These values are $$\cdot L_A(u) = \frac{\alpha_A I_A(u)}{\pi} \tag{10f}$$

Again, using $L_N$ in equation (8a) to normalize the radiance, shows that $L_{cal}^{(N)}$ is a function of u given by $$L_{cal}^{(N)}(u) = \frac{\alpha_A I_A(u)}{\pi L_N} = \frac{\alpha_A I_A(u)}{\alpha K} \quad (10g)$$

Figure 8:
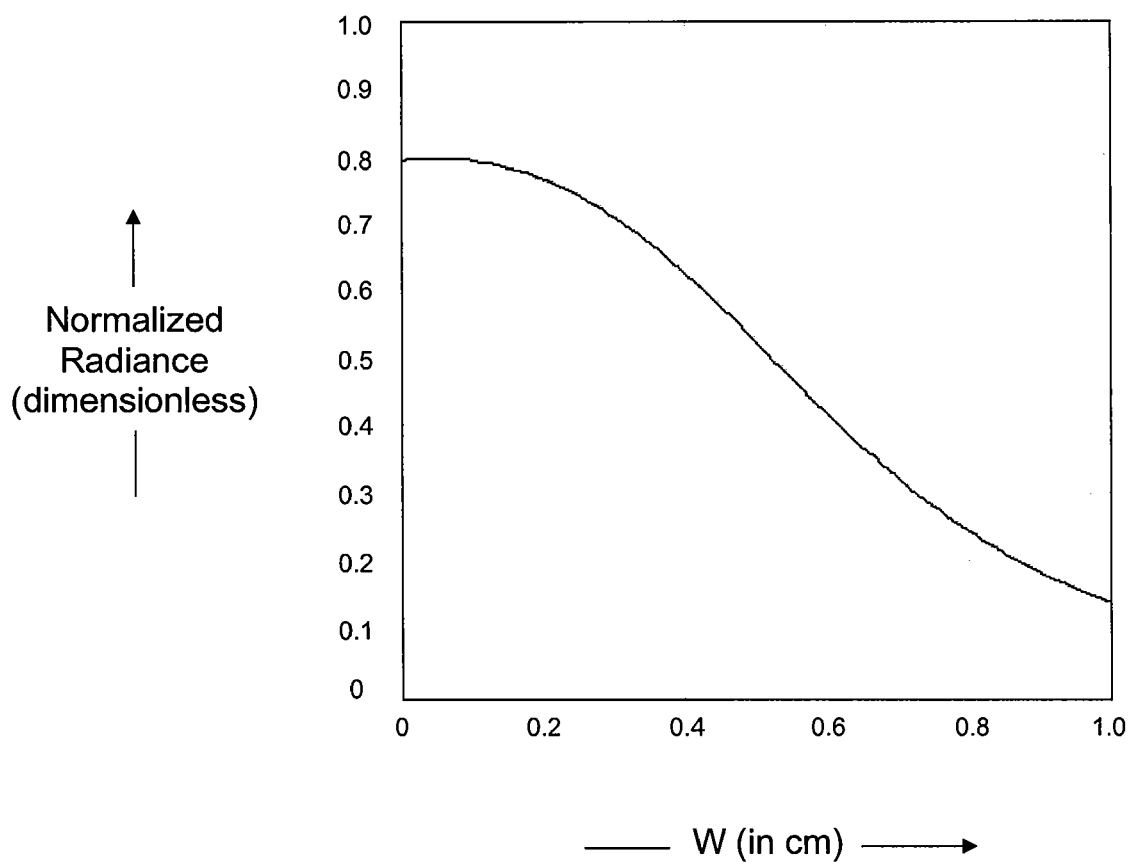
FIG. 8 is a plot of normalized radiance versus the width of the baffles, shown in FIGS. 2a and 2b, when a second surface is specularly reflective and a first surface is lambertian.

FIG. 8 is a plot of $L_{cal}^{(N)}$ against u for $\alpha_A = \alpha_B = \alpha$, where $\alpha$ is the albedo associated with the normalizing radiance $L_N$, produced by the single calibration surface in FIG. 1 and the baffle geometry is specified by equations (8d-8f) and (8h). This has the effect of taking the baffle geometry already analyzed above and replacing the specular surface with a diffusely reflective lambertian surface having the same albedo as the other lambertian surface. The normalized and uniform radiance signal that the sensor observes during calibration is calculated by $$\frac{1}{W}\int_0^W L_{cal}^{(N)}(u)\,du \cong 0.5 \quad (10h)$$

which is substantially less than the normalized and uniform calibration radiances in equations (8i) and (9a). The values of $\alpha_A$ and $\alpha_B$ may always be adjusted to change the value of the calibration radiance. By returning to another type of baffle assembly, with one surface specular and the other lambertian, the calibration radiance may be reduced, if the specularly reflective surface has a specular reflectivity substantially less than one.

In operation, the baffles are removably insertable across the field-of-view (FOV) of the sensor, as shown in FIGS. 2a and 2b. During the operational mode, the sensor is configured to receive reflected radiation from the earth, and the baffles are in their stowed position out of the FOV of the sensor. During the calibration mode, the baffles are moved into their calibration position in the FOV of the imaging sensor. Once in the calibration position, the baffles are inclined with respect to the FOV of the imaging sensor, such that the baffles intercept solar radiation in the FOV of the imaging sensor.

As described above, each baffle has first and second opposing surfaces, with the first surface facing the solar radiation and the second surface facing the sensor, as shown in FIGS. 3a and 3b. One of the two surfaces is configured as a diffused surface, and the other surface is configured as a specular surface. Once inclined, the baffles receive the solar radiation in the FOV of the imaging sensor and reflect the solar radiation from the first surface of a baffle onto the second surface of an adjacent baffle. The solar radiation is reflected from the second surface of the adjacent baffle toward the imaging sensor to allow for calibration of the imaging sensor.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A device for calibrating a sensor using solar radiation comprising
   a sensor configured to measure electromagnetic radiation received through a field of view (FOV) having a normal line of sight,
   a set of at least two baffles, inclined to the line of sight, the baffles removably insertable across the FOV of the sensor, and
   each baffle having first and second opposing surfaces,
   wherein the first surface is disposed to face the solar radiation and the second surface is disposed to face the sensor, and
   either one of the first or second surface is configured as a diffused surface, and
   the other of the first or second surface is configured as a specular surface.

2. The device of claim 1 wherein
   the diffused surface is a Lambertian surface.

3. The device of claim 1 wherein
   the set of baffles is configured to be moved toward a stowed position, away from the FOV of the sensor.

4. The device of claim 1 wherein
   the baffles are hinged to provide a fixed angle between each surface and the line of sight.

5. The device of claim 4 wherein
   the baffles are surrounded by a looped surface, the looped surface providing hinging means for the baffles.

6. The device of claim 1 wherein
   the first and second surfaces each have a width dimension and a length dimension,
   the width dimension is oriented to form an inclination angle to the line of sight, and
   the length dimension is greater than the width dimension.

7. The device of claim 1 wherein
   each baffle is separated from another baffle at a predetermined distance, and
   the predetermined distance is sufficient to allow passage of solar radiation into the FOV of the sensor.

8. The device of claim 7 wherein
   the predetermined distance is smaller than either one of a length dimension or a width dimension of the first and second surfaces.

9. The device of claim 1 wherein
   the line of sight of the sensor is oriented to form an angle less than 90 degrees with respect to rays of the solar radiation.

10. The device of claim 1 wherein
    the diffused surface is a Lambertian surface with an albedo equal to or greater than approximately 0.9, and
    the specular surface has a reflectivity equal to or greater than approximately 0.95.

11. The device of claim 1 wherein
    the set of baffles is configured to be moved toward a stowed position, away from the FOV of the sensor,
    the set of baffles is configured to be moved across the FOV of the sensor during a calibration mode of the sensor,
    the set of baffles forms a virtual image created from the specular surface receiving rays of radiation from the diffused surface, when the set of baffles is in the calibration mode, and
    the virtual image has radiances greater than radiances received by the sensor, when the set of baffles is in the stowed position.

12. A system deployed in orbit around earth including an imaging sensor having a calibration mode and an operational mode, wherein the sensor is configured to receive solar radiation during the calibration mode and reflected radiation from the earth during the operational mode, the system including calibration means for calibrating the imaging sensor comprising
    a set of baffles having a calibration position and a stowed position, wherein the calibration position is configured to intercept solar radiation in the FOV of the imaging sensor, and the stowed position is configured to move the set of baffles away from the FOV of the imaging sensor, and the set of baffles comprising at least two plates inclined with respect to the FOV of the imaging sensor.

13. The system of claim 12 wherein
each plate has two opposing surfaces, one surface having diffusive characteristics and the other surface having specular characteristics.

14. The system of claim 12 wherein
one surface of a first plate is configured to receive radiation from the sun, and the other surface of an adjacent second plate is configured to receive reflected radiation from the one surface of the first plate, and reflect the received reflected radiation toward the imaging sensor during the calibration mode.

15. The system of claim 14 wherein
the one surface of the first plate has either diffusive characteristics or specular characteristics, and the other surface of the adjacent second plate has, respectively, either specular characteristics or diffusive characteristics.

16. The system of claim 12 wherein
each plate has a length dimension and a width dimension, and the length dimension is greater than the width dimension.

17. The system of claim 16 wherein
each plate is separated from an adjacent plate by a predetermined distance, the predetermined distance being smaller than the width dimension.

18. A method of calibrating an imaging sensor disposed in an orbiting satellite comprising the steps of:

moving a set of baffles across a FOV of the imaging sensor, wherein the baffles are tilted with respect to a normal line of sight of the FOV, and each baffle has first and second surfaces;

receiving solar radiation in the FOV of the imaging sensor;

reflecting the solar radiation from the first surface of a baffle onto the second surface of an adjacent baffle;

reflecting the solar radiation from the second surface of the adjacent baffle toward the imaging sensor; and calibrating the imaging sensor using the reflected solar radiation.

19. The method of claim 18 including the step of:
moving the set of baffles away from the FOV of the imaging sensor, after the calibrating step is completed.

20. The method of claim 18 wherein
receiving the solar radiation in the FOV includes receiving the solar radiation at an angle smaller than 90 degrees with respect to the line of sight of the imaging sensor.

* * * * *